United States Patent [19]
Gamblin et al.

[11] Patent Number: 5,552,367
[45] Date of Patent: Sep. 3, 1996

[54] SYNERGISTIC HERBICIDAL COMPOSITIONS COMPRISING 4-BENZOYLISOXAZOLE AND DINITROANILINE HERBICIDES

[75] Inventors: Alan Gamblin; Richard H. Hewett, both of Essex, England

[73] Assignee: Rhone-Poulenc Agriculture Ltd., Ongar, England

[21] Appl. No.: 344,603

[22] Filed: Nov. 18, 1994

[51] Int. Cl.$^6$ .......................... A01N 43/74; A01N 33/18
[52] U.S. Cl. ............................................. 504/138
[58] Field of Search ............................................. 504/138

[56] References Cited

U.S. PATENT DOCUMENTS

| | | | |
|---|---|---|---|
| 4,385,924 | 5/1983 | Theobald et al. | 71/88 |
| 4,500,343 | 2/1985 | Burow, Jr. | 71/76 |
| 5,371,064 | 12/1994 | Cramp et al. | 504/271 |
| 5,374,606 | 12/1994 | Cramp et al. | 504/270 |

FOREIGN PATENT DOCUMENTS

| | | |
|---|---|---|
| 0418175 | 3/1991 | European Pat. Off. . |
| 0487357 | 5/1992 | European Pat. Off. . |
| 0527036 | 2/1993 | European Pat. Off. . |
| 0560482 | 9/1993 | European Pat. Off. . |

OTHER PUBLICATIONS

*Chemical Abstracts*, vol. 121, No. 9, Aug. 29, 1994, Abstract No. 101871 (Pollak et al).
*Chemical Abstracts*, vol. 111, No. 23, Dec. 4, 1989, Abstract No. 210499 (Adamczewski et al).
*The Pesticide Manual*, ninth edition, ed. Charles R. Worthing, The British Crop Protection Council, Surrey, England 1991, pp. 56, 111, 302, 340, 403, 505, 656–657, 706 and 851–852.

Primary Examiner—S. Mark Clardy
Attorney, Agent, or Firm—Burns, Doane, Swecker & Mathis, L.L.P.

[57] ABSTRACT

The invention relates to synergistic compositions comprising:
(a) a 4-benzoylisoxazole of formula (I)

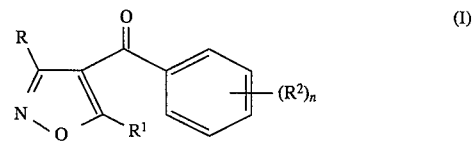

wherein R, R$^1$, R$^2$ and n are as defined in the specification; and
(b) a dinitroaniline herbicide;
and to the use of these compounds as herbicides.

44 Claims, 4 Drawing Sheets

SYNERGISTIC HERBICIDAL COMPOSITIONS COMPRISING 4-BENZOYLISOXAZOLE AND DINITROANILINE HERBICIDES

BACKGROUND OF THE INVENTION

This invention relates to new herbicidal compositions comprising a mixture of 4-benzoylisoxazoles and herbicidal 2,6-dinitroaniline compounds. It also relates to the use of the mixture per se and to a method of controlling weeds.

DISCUSSION OF PRIOR ART 2,6-Dinitroaniline herbicides (hereinafter referred to for convenience as nitroaniline herbicides) are well known in the art and include benfluralin [N-butyl-N-ethyl-2,6-dinitro-4-trifluoromethylbenzenamine], butralin [N-sec-butyl-4-tert-butyl-2,6-dinitroaniline], dinitramine [$N^1,N^1$-diethyl-2,6-dinitro-4 -trifluoromethyl-m-phenylenediamine], ethalfluralin[N-ethyl-N-(2 -methyl-2-propenyl)-2,6-dinitro-4-(trifluoromethyl)benzenamine], fluchloralin [N-(2-chloroethyl)-2,6-dinitro-N-propyl-4 -(trifluoromethyl)aniline], isopropalin [4-isopropyl-2,6-dinitro-N,N-dipropylaniline], pendimethalin [N-(1-ethylpropyl)-3,4-dimethyl- 2,6-dinitrobenzenamine], profluralin [N-cyclopropylmethyl-2,6 -dinitro-N-propyl-4-(trifluoromethyl)benzenamine], and trifluralin [2,6-dinitro-N,N-dipropyl-4-(trifluoromethyl)benzenamine]. Each of these compounds is descibed in for example "The Pesticide Manual", Ninth Edition, edited by C. R. Worthing and published by the British Crop Protection Council, 1991.

Herbicidal 4-benzoylisoxazoles are disclosed in the literature, for example see European Patent Publication Nos. 0418175, 0487357, 0527036 and 0560482.

As a result of research and experimentation it has been found that the use of a nitroaniline herbicide, in combination with certain 4-benzoylisoxazole derivatives, extends the spectrum of herbicidal activity without loss of crop selectivity. Therefore the said combinations represents an important technological advance. The term "combination" as used in this specification refers to the "combination" of a 4-benzoylisoxazole herbicide and a nitroaniline herbicide.

Surprisingly, in addition to this, it has been found that the combined herbicidal activity of certain 4-benzoylisoxazoles with certain nitroaniline herbicides for the control of certain weed species e.g. *Echinochloa crus-galli,* Setaria spp and *Amaranthus retroflexus*, and is greater than expected, without an unacceptable increase in crop phytotoxicity, applied pre- emergence (e.g. as a pre- emergence aqueous spray), i.e. the herbicidal activity of the 4-benzoylisoxazole with a nitroaniline herbicide showed an unexpected degree of synergism, as defined by P. M. L. Tammes, Netherland Journal of Plant Pathology, 70 (1964), pp 73–80 in a paper entitled "Isoboles, a graphic representation of synergism in pesticides".

In addition, the herbicidal activity of the 4-benzoylisoxazole with a nitroaniline herbicide show synergism as defined by Limpel, L. B., P. H. Schuldt and D. Lamont, 1962, 1. Proc. NEWCC 15, 48–53, using the formula:

$$E = X + Y - \frac{X.Y}{100}$$

where

E=the expected percent inhibition of growth by a mixture of two herbicides A and B at defined doses.

X=the percent inhibition of growth by herbicide A at a defined dose.

Y=the percent inhibition of growth by herbicide B at a defined dose.

When the observed percentage of inhibition by the mixture is greater than the expected value E using the formula above the combination is synergistic.

This remarkable synergistic effect gives improved reliability in controlling these competitive weeds of many crop species, leading to a considerable reduction in the mount of active ingredient required for weed control.

A high level of control of these weeds is desirable to prevent:

1) yield loss, through competition and/or difficulties with harvest, 2) crop contamination leading to storage and cleaning difficulties, and 3) unacceptable weed seed return to the soil.

Additionally the invention seeks to provide a herbicidal composition which allows lower dose rates of nitroaniline herbicide to be applied to We environment without reducing (and preferably increasing) the level of weed control.

Also, pendimethalin is known as a selective herbicide which can be applied pre-emergence after seeding in cereals, maize and rice. It is however known that in very wet conditions, the performance of pendimethalin in controlling certain weed species can be significantly reduced; see for example "Crop Protection Chemical Reference, 7th Edition, 1991, Published by Chemical and Pharmaceutical Press, Pages 328–352. Also, under the "Special Precautions" mentioned in the general information on the commercial formulation of pendimethalin "Prowl" (Registered Trade mark), it is stated that excessively wet conditions can reduce weed control). In one aspect the present invention seeks to provide mixtures of pendimethalin with 4-benzoylisoxazole herbicide which provide improved control of weed Species under such conditions and using reduced dose rates of pendimethalin.

DESCRIPTION OF THE INVENTION

The present invention provides a method for controlling the growth of weeds (i.e. undesired vegetation) at a locus which comprises applying to the locus (a) a herbicidally effective mount of a 4-benzoylisoxazole of formula (I):

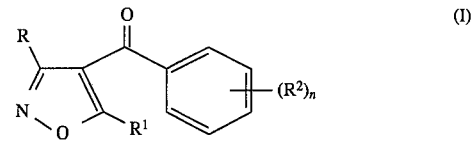

wherein

R is hydrogen or —$CO_2R^3$;

$R^1$ is cyclopropyl;

$R^2$ is selected from halogen, —$S(O)_p$Me and $C_{1-6}$ alkyl or haloalkyl, n is two or three; p is zero, one or two; and $R^3$ is $C_{1-4}$ alkyl; and (b) a herbicidally effective mount of a dinitroaniline herbicide.

Preferably the dinitroaniline herbicide is a compound of the formula II:

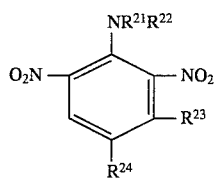

wherein:

R²¹ represents:
straight or branched chain alkyl or alkenyl having up to 12 carbon atoms which may be substituted by one or more halogen atoms or cycloalkyl groups;

R²² represents hydrogen or a group R²¹ as defined above. R²¹ and R²² being the same or different;

R²³ represents:
hydrogen or halogen;
straight or branched chain alkyl having from 1 to 12 carbon atoms which may be substituted by one or more halogen atoms; or
an unsubstituted amino group;

R²⁴ represents:
halogen;
straight or branched chain alkyl having from 1 to 12 carbon atoms which may be substituted by one or more halogen atom;
straight or branched chain alkylsulphonyl having from 1 to 12 carbon atoms which may be substituted by one or more halogen atoms;
or sulphamoyl.

For this purpose, the nitroaniline herbicide and 4-benzoylisoxazole are normally used in the form of herbicidal compositions (i.e. in association with compatible diluents or carriers and/or surface-active agents suitable for use in herbicidal compositions), for example as hereinafter described.

Preferred compounds of formula II include those wherein R²¹ is selected from the group consisting of ethyl, propyl, butyl, 1-ethylpropyl, 2-methyl-1-propenyl, cyclopropylmethyl and 2-chloroethyl.

Preferred compounds of formula II include those wherein R²² is selected from hydrogen, ethyl and propyl.

Preferred compounds of formula II include those wherein R²³ is selected from hydrogen, methyl and unsubstituted amino.

Preferred compounds of formula II include those wherein R²⁴ is selected from methyl, tert-butyl, isopropyl and trifluoromethyl.

Especially preferred compounds of formula II are:
N-butyl-N-ethyl-2,6-dinitro-4-(trifluoromethyl)benzenamine;
N-sec-butyl-tert-butyl-2,6-dinitroaniline;
N¹,N¹-diethyl-2,6-dinitro-4-trifluoromethyl-m-phenylenediamine;
N-ethyl-N-(2-methyl-2-propenyl)-2,6-dinitro-4 -(trifluoromethyl)benzenamine;
N-(2-chloroethyl)-2,6-dinitro-N-propyl-4 -(trifluoromethyl)aniline;
4-isopropyl-2,6-dinitro-N,N-dipropylaniline;
N-cyclopropylmethyl-2,6-dinitro-N-propyl-4 -(trifluoromethyl)benzenamine;
2,6-dinitro-N,N-dipropyl-4-(trifluoromethyl)benzeneamine and
N-(1-ethylpropyl)-3,4-dimethyl-2,6-dinitrobenzeneamine,
the last two of which are known respectively as trifluralin and pendimethalin and are particularly preferred, pendimethalin being most preferred.

In formula (I) above, compounds in which n is three and the groups $(R^2)_n$ occupy the 2,3 and 4-position of the benzoyl ring; or in which n is two and the groups $(R^2)_n$ occupy the 2- and 4-positions of the benzoyl ring are preferred.

In formula (I) above, preferably R² is selected from chlorine, bromine, —$S(O)_p$Me and trifluoromethyl.

In formula (I) above, preferably one of the groups R² is —$S(O)_p$Me.

Compounds of formula (I) in which R is hydrogen are also preferred.

Compounds of formula (I) of particular interest include the following:

A 5-cyclopropyl-4-(2-methylsulphonyl-4-trifluoromethyl)benzoylisoxazole;
B 5-cyclopropyl-4-(4-methylsulphonyl-2-trifluoromethyl)benzoylisoxazole;
C 4-(2-chloro-4-methylsulphonyl)benzoyl-5-cyclopropylisoxazole;
D 4-(4-chloro-2-methylsulphonyl)benzoyl- 5-cyclopropylisoxazole;
E 4-(4-bromo-2-methylsulphonyl)benzoyl-5-cyclopropylisoxazole;
F ethyl 3-[5-cyclopropyl-4-(3,4-dichloro-2methylsulphenyl)benzoylisoxazole]carboxylate; and
G 5-cyclopropyl-4-(3,4-dichloro-2-methylsulphonyl)benzoylisoxazole.

The letters A to G are assigned to these compounds for reference and identification hereafter.

Compounds A, B and D are preferred, with A being particularly preferred.

The mounts of the nitroaniline herbicide and 4-benzoylisoxazole applied vary depending on the weeds present and their population, the compositions used, the timing of the application, the climatic and edaphic conditions, and (when used to control the growth of weeds in crop growing areas) the crop to be treated. In general, taking these factors into account, application rates from 0.5 g to 512 g of 4-benzoylisoxazole and from 8 g to 3000 g of the nitroaniline herbicide per hectare give good results. However, it will be understood that higher or lower application rates may be used, depending upon the problem of weed control encountered.

For the selective control of weeds at a locus of weed infestation which is an area used, or to be used, for growing of crops application rates from 5 g to 512 g of 4-benzoylisoxazole and from 150 g to 3000 g of the nitroaniline herbicide per hectare are particularly suitable, preferably from 20 g to 200 g of 4-benzoylisoxazole and from 150 g to 2000 g of the nitroaniline herbicide per hectare, most preferably from 25 g to 150 g of 4-benzoylisoxazole and from 250 g to 500 g of the nitroaniline herbicide per hectare.

When applied to a crop-growing area, the rate of application should be sufficient to control the growth of weeds without causing substantial permanent damage to the crop.

By the term 'pre-emergence application' is meant application to the soft in which the weed seeds or seedlings are present before emergence of the crop. One example of a pre-emergence application is known as 'pre-plant incorporated' (PPI), where the herbicide is incorporated into the soil before planting the crop. Another is where the herbicide is applied to the soil surface after sowing the crop. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soft, are controlled.

In the present invention, PPI or pre-emergence applications are preferred, and pre-emergence application of the 4-benzoylisoxazole and nitroaniline herbicide is most preferred.

Preferably the combination of 4-benzoylisoxazole and nitroaniline herbicide is applied to an area used, or to be used, for the growing of a crop, for example maize, sugarcane or plantation crops. Preferably the crop is maize.

In accordance with the usual practice, a tank mix may be prepared prior to use by combining separate formulations of the individual herbicidal components.

The following non-limiting experiments illustrate the present invention.

EXPERIMENTAL PROCEDURE A

Seed of the various species of broad-leaf or grass weeds were sown in unsterilised clay loam soil in 7 centimeter by 7 centimeter plastic plant pots. The pots were watered and allowed to drain, The soil surface was then sprayed with ranges of concentrations of either the individual herbicide or mixtures of two herbicides in various proportions, dissolved in a 50:50 by volume solution of acetone and water, using a track sprayer set to deliver the equivalent of 290 l/ha. The herbicides were used as unformulated technical materials.

Treated pots were placed at random in four replicate blocks per treatment for each plant species. The pots were held, in a glasshouse, standing on moist capillary matting, under lights and with overhead watering twice daily.

Two weeks after treatment the percent reduction in plant growth, compared to an untreated control, was assessed.

Mean percent reduction in plant growth was calculated for each treatment. Dose/mean response was plotted on Log concentration/Probability graph paper, and lines fitted by eye. For herbicide mixtures a dose/response line for the first herbicide was drawn for each dose rate of the second herbicide and a dose/response line for the second herbicide was drawn for each dose rate of the first herbicide. The doses representing a 90% reduction in plant growth (LD90 values) were read from these lines and plotted on graphs whose axes were dose rates of the two herbicides. The line joining these points is an Isobole i.e. a line joining points (mixtures) of equal activity, as described by P. M. L. Tammes, Neth. J. Plant Path. 70 (1964): 73–80. A line was also drawn joining the LD90 values of the individual components of the mixture, This line represents the theoretical isobole if the effect of the two components is additive i.e. there is no interaction between them. Isoboles falling below this line indicate synergy between the components while lines lying above it indicate antagonism.

In the tables that follow 'dose' represents the dose rate in grammes per hectare of the active ingredient used; and the figures for the weed control are percentages reduction in growth when compared with the untreated controls.

Results:

TABLE A1

Pre-Emergence treatment of Echinochloa crus-galli with various mixtures of Compound A and pendimethalin

| Cpd. | Dose | Pendimethalin | | | | | | |
|------|------|---|---|---|---|---|---|---|
|      |      | 0 | 8 | 16 | 32 | 64 | 128 | 256 |
| A | 0 | — | 0.83 | 0.83 | 0.83 | 0.83 | 0.83 | 77.42 |
|   | 0.5 | 0 | 1.67 | 0 | 1.67 | 5.83 | 21.17 | 54.08 |
|   | 1 | 1.67 | 0.83 | 0.83 | 0.83 | 0.83 | 13.5 | 40.58 |
|   | 2 | 1.67 | 5 | 1.67 | 8.5 | 7.5 | 2.08 | — |
|   | 4 | 2.5 | 0.83 | 2.5 | 5 | 6.42 | 41.92 | 61.42 |
|   | 8 | 16.33 | 30.92 | 7 | 37.42 | 27.17 | 72.42 | 90.25 |
|   | 16 | 51.92 | 59.25 | 60.83 | 77.5 | 82.42 | 90.58 | 99.92 |
|   | 32 | 76.83 | 95.67 | 91.58 | 88.5 | 97.83 | 85 | 98.17 |
|   | 64 | 97 | 99.08 | 98.17 | 99.92 | 98.67 | 97.75 | 97.58 |
|   | 128 | 98.67 | 100 | 99.17 | 99.92 | 100 | 99 | 99.92 |

TABLE A2

Pre-Emergence treatment of Setaria faberi with various mixtures of Compound A and pendimethalin

| Cpd. | Dose | Pendimethalin | | | | | | |
|------|------|---|---|---|---|---|---|---|
|      |      | 0 | 8 | 16 | 32 | 64 | 128 | 256 |
| A | 0 | — | 2.92 | 33.08 | 37 | 60.75 | 86 | 94.83 |
|   | 0.5 | 3.25 | 14.83 | 47.25 | 30.58 | 63.08 | 94.5 | 93.5 |
|   | 1 | 6.33 | 17.42 | 41.5 | 35.5 | 48.5 | 66 | 85.67 |
|   | 2 | 2.17 | 4.75 | 28.5 | 22.75 | 19.42 | 81.83 | — |
|   | 4 | 23.17 | 12.75 | 10.17 | 39.5 | 59.5 | 79.83 | 90.67 |
|   | 8 | 18.42 | 39 | 45.25 | 40.58 | 69.92 | 87.83 | 93.5 |
|   | 16 | 39.58 | 27.5 | 50.67 | 62.83 | 70.83 | 86.42 | 97.08 |
|   | 32 | 64.5 | 33.17 | 67.83 | 68.92 | 77.42 | 91.75 | 96.5 |
|   | 64 | 76.42 | 90.5 | 83.08 | 88.67 | 89.25 | 94.67 | 98.33 |
|   | 128 | 90.17 | 95.5 | 83.25 | 86.33 | 91.75 | 98.83 | 98.33 |

TABLE A3

Pre-Emergence treatment of Setaria viridis with various mixtures of Compound A and pendimethalin

| Cpd. | Dose | Pendimethalin | | | | | | |
|------|------|---|---|---|---|---|---|---|
|      |      | 0 | 8 | 16 | 32 | 64 | 128 | 256 |
| A | 0 | — | 8.33 | 31.42 | 62.5 | 82.83 | 91 | 97.67 |
|   | 0.5 | 0 | 29.83 | 38.08 | 63.08 | 86.92 | 93.83 | 97 |
|   | 1 | 2.83 | 7.83 | 42.75 | 67 | 89.42 | 85.5 | 95.17 |
|   | 2 | 0 | 9.17 | 37.42 | 52.17 | 85.67 | 91.92 | — |
|   | 4 | 3.08 | 31.17 | 23.92 | 67.42 | 92.17 | 88.33 | 94.5 |
|   | 8 | 8.33 | 17.42 | 44.75 | 72.5 | 87 | 89.58 | 96 |
|   | 16 | 28.25 | 12.25 | 70.5 | 77.25 | 89.5 | 94.92 | 98.75 |
|   | 32 | 54 | 63.42 | 79.5 | 95.08 | 95.17 | 96.75 | 98 |
|   | 64 | 84.75 | 79.75 | 82.67 | 95.58 | 99.08 | 99.92 | 100 |
|   | 128 | 94.75 | 89.33 | 95.58 | 95.17 | 98.42 | 99.25 | 99.92 |

TABLE A4

Pre-Emergence treatment of Amaranthus retroflexus with various mixtures of Compound A and pendimethalin

| Cpd. | Dose | Pendimethalin | | | | | |
|------|------|---|---|---|---|---|---|
|      |      | 0 | 31.25 | 62.5 | 125 | 250 | 500 |
| A | 0 | — | 10 | 2.5 | 7.5 | 12.5 | 53.75 |
|   | 1 | 0 | 47.5 | 52.5 | 39.75 | 72.5 | 48.75 |
|   | 2 | 46.25 | 27.5 | 53.75 | 62.5 | 62.5 | 63.75 |
|   | 4 | 57.5 | 66.25 | 60 | 75 | 77.5 | 73.75 |
|   | 8 | 80 | 72.75 | 85 | 93.75 | 78.75 | 92.5 |
|   | 16 | 78.5 | 71.25 | 88.75 | 90 | 95 | 90 |

TABLE A4-continued

Pre-Emergence treatment of *Amaranthus retroflexus* with various mixtures of Compound A and pendimethalin

| Cpd. | Dose | Pendimethalin | | | | | |
|---|---|---|---|---|---|---|---|
| | | 0 | 31.25 | 62.5 | 125 | 250 | 500 |
| | 32 | 93.75 | 98.75 | 96 | 92.5 | 92.5 | 97.25 |
| | 64 | 98.75 | 98.25 | 98.75 | 98.75 | 100 | 96.25 |

The results above clearly demonstrate the excellent and unexpected degree of synergism obtained with the combination of the invention.

Figure 1:
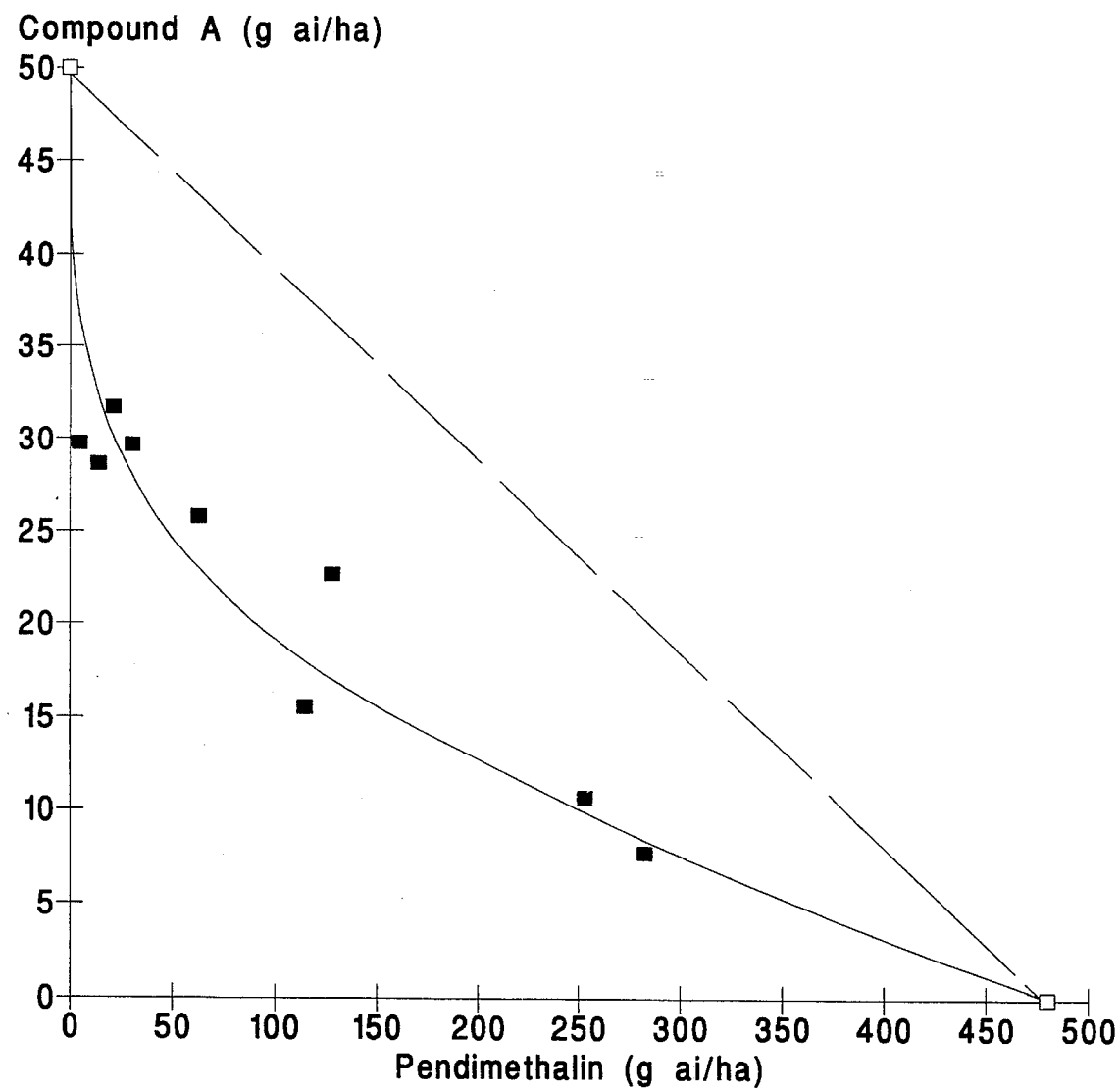
FIG. 1 is an LD90 isobole plot calculated from observed values (-■-) and a corresponding plot of expected additive values (dashed line) for a range of mixtures of Compound A with pendimethalin against the weed species *Echinochloa crus-galli*, produced from the results shown in Table A1.
Figure 2:
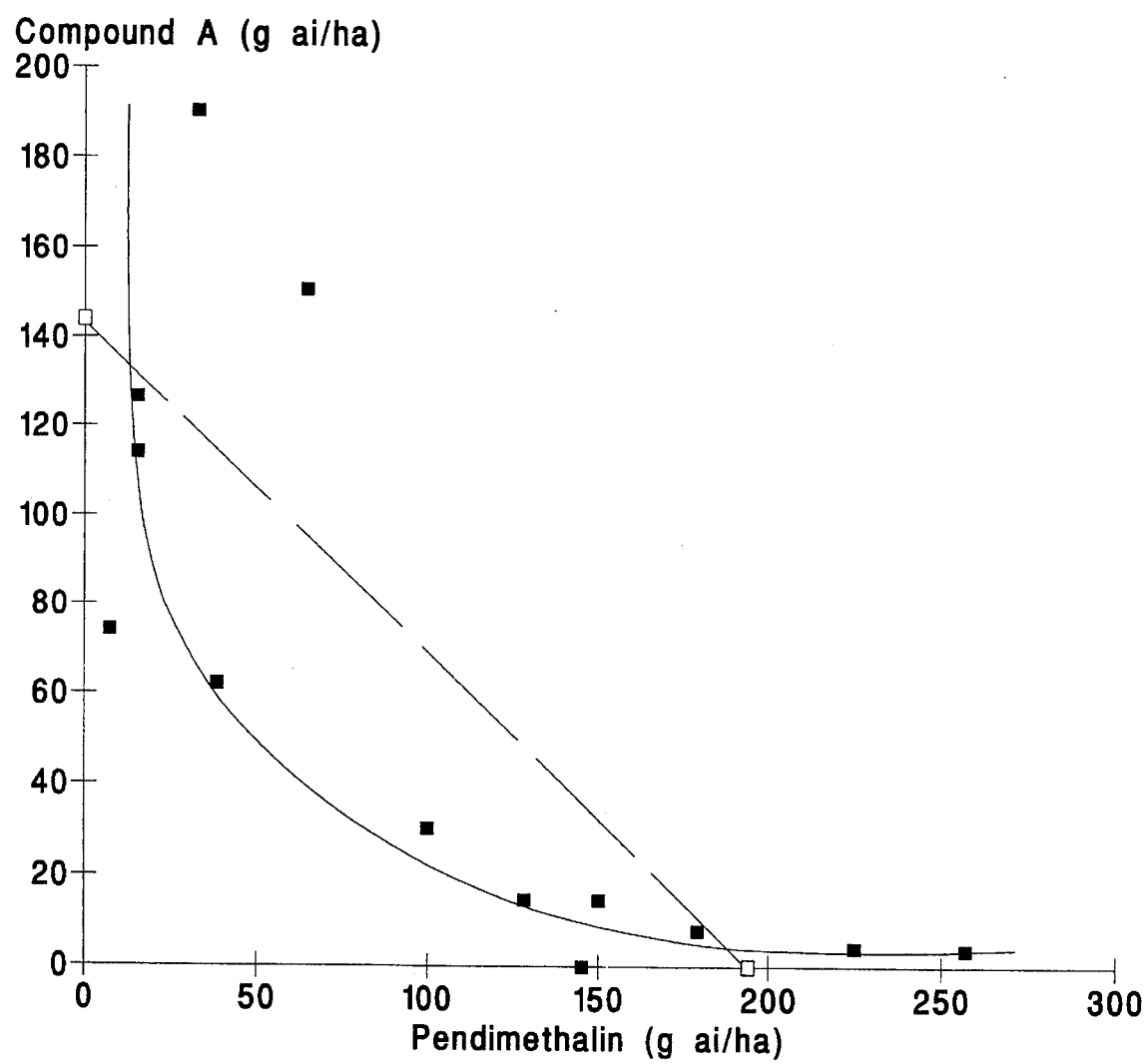
FIG. 2 is an LD90 isobole plot calculated from observed values (-■-) and a corresponding plot of expected additive values (dashed line) for a range of mixtures of Compound A with pendimethalin against the weed species *Setaria faberi*, produced from the results shown in Table A2.
Figure 3:
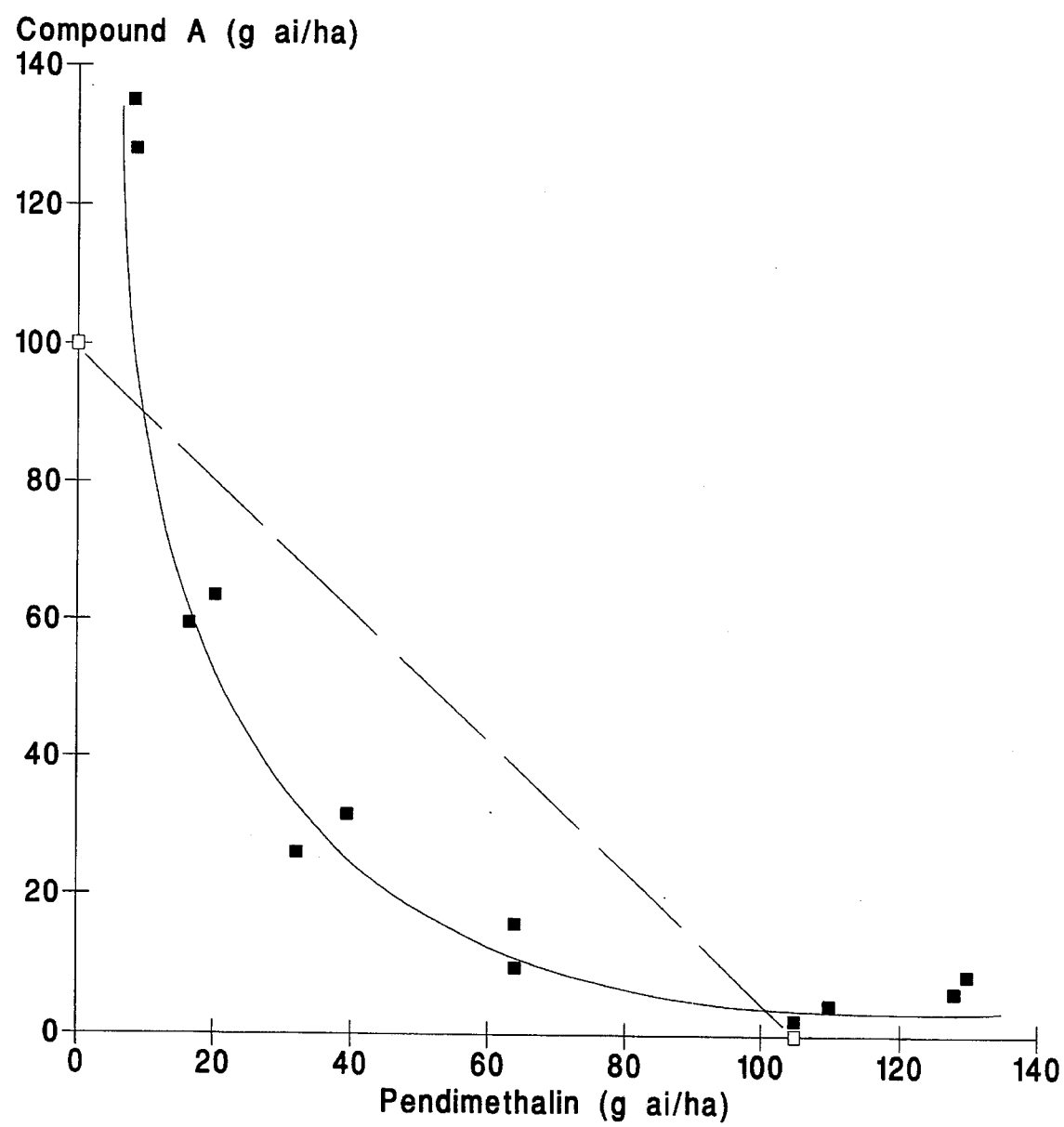
FIG. 3 is an LD90 isobole plot calculated from observed values (-■-) and a corresponding plot of expected additive values (dashed line) for a range of mixtures of Compound A with pendimethalin against the weed species *Setaria viridis*, produced from the results shown in Table A3.
Figure 4:
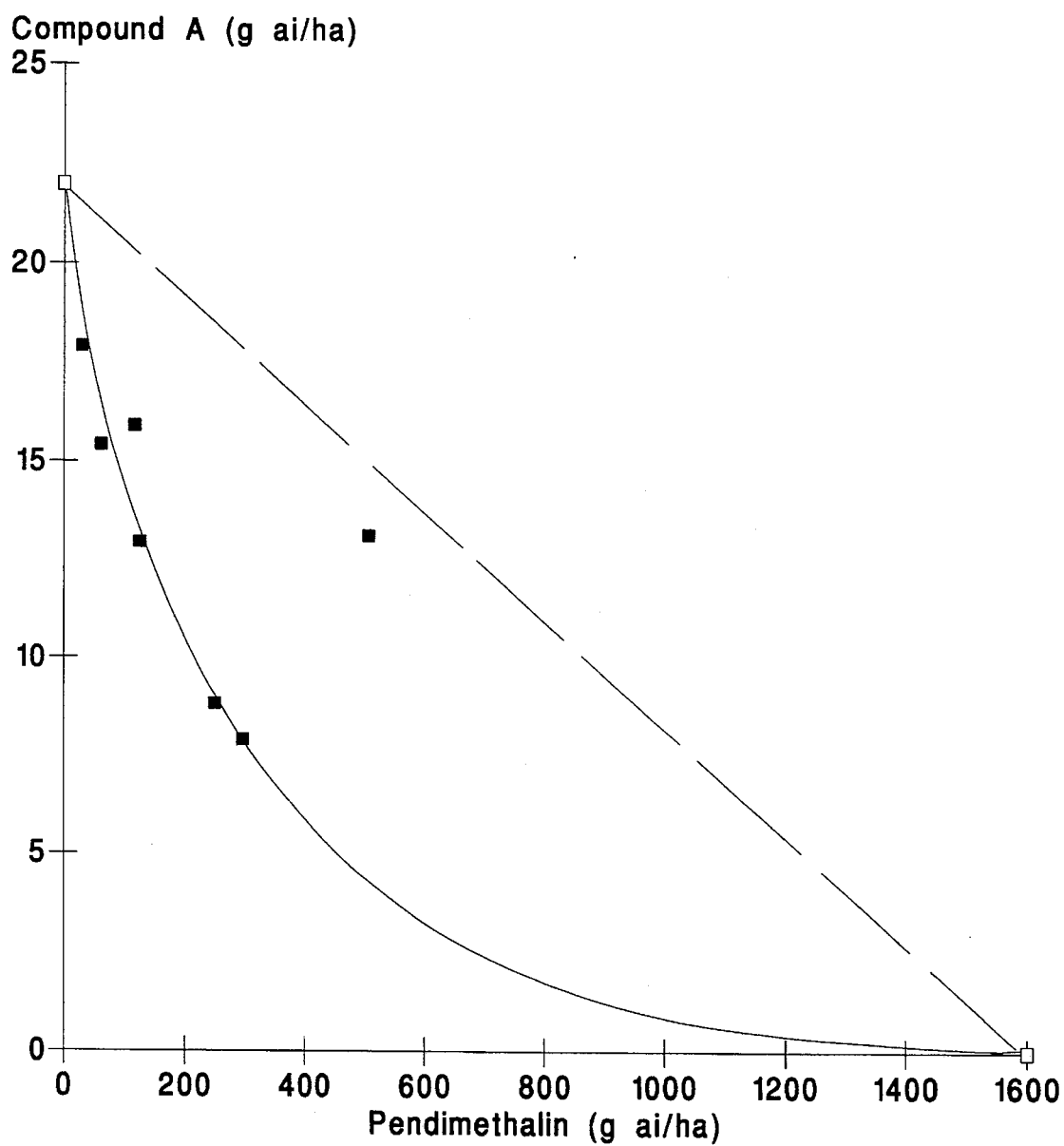
FIG. 4 is an ID90 isobole plot calculated from observed values (-■-) and a corresponding plot of expected additive values (dashed line) for a range of mixtures of Compound A with pendimethalin against the weed species *Amaranthus retroflexus*, produced from the results shown in Table A4.

The isoboles produced from the above data, shown hereinafter in FIGS. 1–4 were clearly type III curves (Tammes op. cit., Page 75, FIG. 2) characteristic of synergism.

EXPERIMENTAL PROCEDURE B

The experiments were carded out pre-emergence of the weed species at (i) a research farm in Brazil with Compound B (formulated as a wettable powder) and pendimethalin, (formulated as a suspension concentrate); and (ii) in research farms in the Mid West corn belt of the United States with compound A (formulated as a wettable powder) and pendimethalin (formulated as a emulsifiable concentrate), A solution of the two active ingredients (a.i.) was mixed for one hour and applied at a spray volume of 231 liters/hectare to a 3 meter by 5 meter test plot comprising the weed species which were sown 2 days earlier, 3 replicates were performed. A control plot was sprayed with a solution not containing test compound, Visual assessment of phytotoxicity was made after 36 or 40 days from sowing each weed species based on a comparison with the control plot.

The tables below show the observed percentage control of the weed species by each combination, with the figure in brackets representing the predicted value using the Limpel formula, The dose rates are in grammes per hectare.

TABLE B1

Pre-Emergence treatment of *Amaranthus retroflexus* with various mixtures of Compound B and pendimethalin

| | | Pendimethalin | |
|---|---|---|---|
| Cpd | Dose (g/ha) | 0 | 350 |
| B | 0 | — | 28 |
| | 37.5 | 38 | 82(55) |

TABLE B2

Pre-Emergence treatment of *Panicum muticum* with various mixtures of Compound A and pendimethalin

| | | Pendimethalin | |
|---|---|---|---|
| Cpd | Dose (g/ha) | 0 | 350 |
| A | 0 | — | 5 |
| | 37.5 | 65 | 88(67) |

TABLE B3

Pre-Emergence treatment of *Setaria viridis* with various mixtures of Compound A and pendimethalin

| | | Pendimethalin | |
|---|---|---|---|
| Cpd | Dose (g/ha) | 0 | 350 |
| A | 0 | — | 27 |
| | 37.5 | 63 | 99(73) |

TABLE B4

Pre-Emergence treatment of *Setaria faberi* with various mixtures of Compound A and pendimethalin

| | | Pendimethalin | |
|---|---|---|---|
| Cpd | Dose (g/ha) | 0 | 350 |
| A | 0 | — | 32 |
| | 37.5 | 85 | 99(90) |

TABLE B4

Pre-Emergence treatment of *Setaria faberi* with various mixtures of Compound A and pendimethalin

| | | Pendimethalin | |
|---|---|---|---|
| Cpd | Dose (g/ha) | 0 | 350 |
| A | 0 | — | 25 |
| | 37.5 | 62 | 99(72) |

EXPERIMENTAL PROCEDURE C

The experiments were carried out pre-emergence of the weed species at a research farm locations in the Mid-West corn belt in United States of America with to determine the selectivity of the combination in maize using Compound A (formulated as a wettable powder) and pendimethalin (formulated as a 96% emulsifiable concentrate).

Various mixtures of compound A and pendimethalin were weighed out and dissolved in water to give a solution containing the appropriate concentrations and ratios of active ingredients.

The solution was mixed for one hour and applied at a spray volume of 231 liters/hectare to a 3 meter by 5 meter test plot comprising the maize seed which were sown 2 days earlier. 3 replicates were performed. The experiments were performed using seven varieties of maize. A control plot was sprayed with a solution not containing test compound. Visual assessment of phytotoxicity was made 40 days after sowing the maize seeds based on a comparison with the control plot.

TABLE C1

Field trial showing the biological interaction between Compound A and pendimethalin on maize

| Cpd | Dose | Pendimethalin | | |
|---|---|---|---|---|
| | | 0 | 560 | 1120 |
| A | 0 | — | — | — |
| | 78 | 0 | 0 | 0 |
| | 105 | 0 | 0 | 0 |

According to a further feature of the present invention there are provided herbicidal compositions comprising (a) a 4-benzoylisoxazole derivative of formula I as defined above; and (b) a nitroaniline herbicide;

in association with, and preferably homogeneously dispersed in a herbicidally acceptable diluent or carrier and/or surface active agent.

The term "herbicidal composition" is used in a broad sense, to include not only compositions which are ready for use as herbicides but also concentrates which must be diluted before use. Preferably, the compositions contain from 0.05 to 90% by weight of 4-benzoylisoxazole and nitroaniline herbicide, Unless otherwise stated, the percentages and ratios appearing in this specification are by weight.

Generally a composition in which the ratio of (a):(b) is from 1:6000 to 64:1 wt/wt of (a); (b) is used, proportions from 1:600 to 3.41:1 wt/wt being preferred, with proportions from 1:100 to 1.33:1 wt/wt particularly preferred and proportions of from 1:20 to 1:1.33 wt/wt especially preferred.

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. Examples of suitable liquid diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

The wettable powders (or powders for spraying) usually contain from 20 to 95% of 4-benzoylisoxazole and nitroaniline herbicide, and they usually contain, in addition to the solid vehicle, from 0 to 5% of a wetting agent, from 3 to 10% of a dispersant agent and if necessary, from 0 to 10% of one or more stabilisers and/or other additives such as penetrating agents, adhesives or anti-caking agents and colourings.

The aqueous suspension concentrates, which are applicable by spraying, are prepared in such a way as to obtain a stable fluid product (by fine grinding) which does not settle out and they usually contain from 10 to 75% of 4-benzoylisoxazole and nitroaniline herbicide, from 0.5 to 15% of surface acting agents, from 0.1 to 10% of thixotropic agents, from 0 to 10% of suitable additives such as antifoams, corrosion inhibitors, stabilisers, and water or an organic liquid in which the active substance is sparingly soluble or insoluble. Some organic solid substances or inorganic salts can be dissolved in order to assist in preventing sedimentation or as antifreeze for the water.

Preferred herbicidal compositions according to the present invention are wettable powders and water-dispersible granules.

Herbicidal compositions according to the present invention may also comprise a 4-benzoylisoxazole and a nitroaniline in association with, and preferably homogeneously dispersed in, one or more other pesticidally active compounds and, if desired one or more compatible pesticidally acceptable diluents and carriers. Preferred herbicidal compositions according to the present invention are those which comprise a 4-benzoylisoxazole and a nitroaniline herbicide in association with other herbicides.

The compositions of the invention may be made up as an article of manufacture comprising a 4-benzoylisoxazole and a nitroaniline herbicide and optionally other pesticidally active compounds as hereinbefore described, and as is preferred, a herbicidal composition as hereinbefore described and preferably a herbicidal concentrate which must be diluted before use, comprising the 4-benzoylisoxazole and nitroaniline within a container for the aforesaid 4-benzoylisoxazole and nitroaniline or a said herbicidal composition and instructions physically associated with the aforesaid container, setting out the manner in which the aforesaid 4-benzoylisoxazole and nitroaniline or herbicidal composition contained therein, is to be used to control the growth of weeds. The containers will normally be of the types conventionally used for the storage of chemical substances and concentrated herbicidal compositions, which are solids or liquids at normal ambient temperatures, for example cans and drams of plastics materials or metal (which may be internally-lacquered), bottles of glass and plastics materials; and when the contents of the container is a solid, for example a granular herbicidal composition, boxes, for example of cardboard, plastics material, metal or sacks. The containers will normally be of sufficient capacity, to contain amounts of the active ingredients or herbicidal compositions sufficient to treat at least one hectare of ground, to control the growth of weeds therein but will not exceed a size which is convenient for conventional methods of handling. Instructions will be physically associated with the container, for example by being printed directly thereon or on a label or tag affixed thereto. The directions will normally indicate that the contents of the container, after dilution if necessary, are to be applied to control the growth of weeds at rates of application from 0.5 to 512 g of 4-benzoylisoxazole and from 8 to 3000 g of nitroaniline herbicide per hectare in the manner and for the purpose hereinbefore described.

The processes described in European Patent Publication Nos. 0418175, 0487357, 0527036 and 0560482 may be used to prepare the compounds of formula (I).

According to a further feature of the present invention, there is provided a product comprising (a) 4-benzoylisoxazole of formula I above and (b) a nitroaniline herbicide, as a combined preparation for simultaneous, separate or sequential use in controlling the growth of weeds at a locus.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

We claim:

1. A synergistic herbicidal product comprising a synergistic herbicidally effective amount of:

(a) a 4-benzoylisoxazole of formula (I):

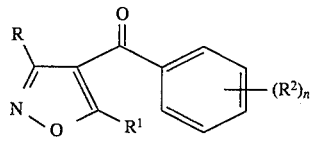

wherein

R is hydrogen or —$CO_2R^3$;

$R^1$ is cyclopropyl;

$R^2$ is selected from the group consisting of halogen, —$S(O)_p$Me, $C_{1-6}$ alkyl and $C_{1-6}$ haloalkyl;

n is two or three;

p is zero, one or two; and $R^3$ is $C_{1-4}$ alkyl; and (b) a dinitroaniline herbicide;

as a combined preparation for simultaneous, separate or sequential use in controlling the growth of weeds at a locus;

wherein the weight ratio of (a):(b) is from 1:6000 to 64:1.

2. A synergistic herbicidal composition comprising a synergistic herbicidally effective amount of:

(a) a 4-benzoylisoxazole of formula (I):

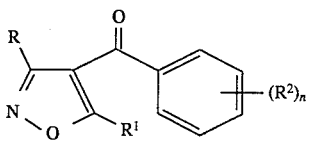

wherein

R is hydrogen or —$CO_2R^3$;

$R^1$ is cyclopropyl;

$R^2$ is selected from the group consisting of halogen, —$S(O)_p$Me, $C_{1-6}$ alkyl and $C_{1-6}$ haloalkyl;

n is two or three;

p is zero, one or two; and $R^3$ is $C_{1-4}$ alkyl; and (b) a dinitroaniline herbicide;

in association with one or more members selected from the group consisting of a herbicidally acceptable diluent or carrier and a herbicidally acceptable surface active agent;

wherein the weight ratio of (a):(b) is from 1:6000 to 64:1.

3. The composition according to claim 2 in which the dinitroaniline herbicide is a compound of formula II:

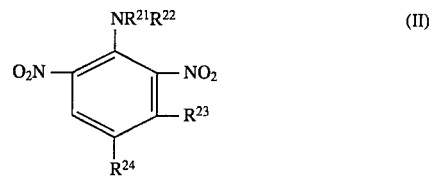

wherein:

$R^{21}$ represents:
   straight or branched chain alkyl or alkenyl having up to 12 carbon atoms which may be substituted by one or more halogen atoms or cycloalkyl groups;

$R^{22}$ represents hydrogen or a group $R^{21}$ as defined above, $R^{21}$ and $R^{22}$ being the same or different;

$R^{23}$ represents:
   hydrogen or halogen;
   straight or branched chain alkyl having from 1 to 12 carbon atoms which may be substituted by one or more halogen atoms; or
   an unsubstituted amino group;

$R^{24}$ represents:
   halogen;
   straight or branched chain alkyl having from 1 to 12 carbon atoms which may be substituted by one or more halogen atoms;
   straight or branched chain alkylsulphonyl having from 1 to 12 carbon atoms which may be substituted by one or more halogen atoms;
   or sulphamoyl.

4. The composition according to claim 3 wherein $R^{21}$ is selected from the group consisting of ethyl, propyl, butyl, 1-ethylpropyl, 2-methyl-1-propenyl, cyclopropylmethyl and 2-chloroethyl.

5. The composition according to claim 3 wherein $R^{22}$ is selected from hydrogen, ethyl and propyl.

6. The composition according to claim 3 wherein $R^{23}$ is selected from hydrogen, methyl and unsubstituted amino.

7. The composition according to claim 3 wherein $R^{24}$ is selected from methyl, tert-butyl, isopropyl and trifluoromethyl.

8. The composition according to claim 2 wherein the dinitroaniline herbicide is selected from the group consisting of N-butyl-N-ethyl-2,6-dinitro-4-(trifluoromethyl)benzenamine;

N-sec-butyl-4-tert-butyl-2,6-dinitroaniline;

$N^1,N^1$-diethyl-2,6-dinitro-4-trifluoromethyl-m-phenylenediamine;

N-ethyl-N-(2-methyl-2-propenyl)-2,6-dinitro-4-trifluoromethyl)benzenamine;

N-(2-chloroethyl)-2,6-dinitro-N-propyl-4-trifluoromethyl)aniline;

4-isopropyl-2,6-dinitro-N,N-dipropylaniline;

N-cyclopropylmethyl-2,6-dinitro-N-propyl-4-trifluoromethyl)benzenamine;

2,6-dinitro-N,N-dipropyl-4-(trifluoromethyl)benzeneamine; and

N-(1-ethylpropyl)-3,4-dimethyl-2,6-dinitrobenzeneamine.

9. The composition according to claim 2 wherein for the compound of formula I, n is three and the groups $(R^2)_n$ occupy the 2,3 and 4-positions of the benzoyl ring, wherein $R^2$ is as defined in claim 2.

10. The composition according to claim 2 wherein for the compound of formula I, n is two and the groups $(R^2)_n$ occupy the 2 and 4-positions of the benzoyl ring, wherein $R^2$ is as defined in claim 2.

11. The composition according to claim 2 wherein for the compound of formula I, $R^2$ is selected from chlorine, bromine, —S(O)$_p$Me and trifluoromethyl, wherein p is as defined in claim 2.

12. The composition according to claim 2 wherein for the compound of formula I, one of the groups $R^2$ is —S(O)$_p$Me, wherein p is as defined in claim 2.

13. The composition according to claim 2 wherein for the compound of formula I, R is hydrogen.

14. The composition according to claim 2 wherein the compound of formula I is selected from the group consisting of
5-cyclopropyl-4-(2-methylsulphonyl-4-trifluoromethyl) benzoylisoxazole;
5-cyclopropyl-4-(4-methylsulphonyl-2-trifluoromethyl) benzoylisoxazole;
4-(2-chloro-4-methylsulphonyl)benzoyl-5-cyclopropylisoxazole;
4-(4-chloro-2-methylsulphonyl)benzoyl-5-cyclopropylisoxazole;
4-(4-bromo-2-methylsulphonyl)benzoyl-5-cyclopropylisoxazole;
ethyl 3-[5-cyclopropyl-4-(3,4-dichloro-2-methylsulphenyl) benzoylisoxazole]carboxylate; and
5-cyclopropyl-4-(3,4-dichloro-2-methylsulphonyl)benzoylisoxazole.

15. The composition according to claim 2 wherein the compound of formula I is 5-cyclopropyl-4-(2-methylsulphonyl-4-trifluoromethyl)benzoylisoxazole.

16. The composition according to claim 2 wherein the weight ratio of (a):(b) is from 1:600 to 3.41:1.

17. The composition according to claim 2 wherein the weight ratio of (a):(b) is from 1:100 to 1.33:1.

18. The composition according to claim 2 wherein the weight ratio of (a):(b) is from 1:20 to 1:1.33.

19. The composition according to claim 2 in the form of a wettable powder or a water-dispersible granule.

20. A method for controlling the growth of weeds at a locus which comprises applying to the locus a synergistic herbicidally effective amount of:
(a) a 4-benzoylisoxazole of formula (I):

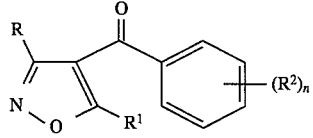

wherein
R is hydrogen or —CO$_2$R$^3$;
$R^1$ is cyclopropyl;
$R^2$ is selected from the group consisting of halogen, —S(O)$_p$Me, $C_{1-6}$ alkyl and $C_{1-6}$ haloalkyl;
n is two or three;
p is zero, one or two; and
$R^3$ is $C_{1-4}$ alkyl; and
(b) a dinitroaniline herbicide;
wherein from 0.5 g to 512 g of said 4-benzoylisoxazole of formula (I) and from 8 g to 3000 g of said dinitroaniline herbicide per hectare are applied to said locus.

21. The method according to claim 20 in which the dinitroaniline herbicide is a compound of formula II:

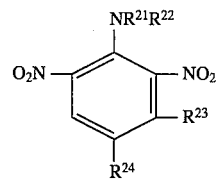

wherein:
$R^{21}$ represents:
straight or branched chain alkyl or alkenyl having up to 12 carbon atoms which may be substituted by one or more halogen atoms or cycloalkyl groups;
$R^{22}$ represents hydrogen or a group $R^{21}$ as defined above, $R^{21}$ and $R^{22}$ being the same or different;
$R^{23}$ represents:
hydrogen or halogen;
straight or branched chain alkyl having from 1 to 12 carbon atoms which may be substituted by one or more halogen atoms; or
an unsubstituted amino group;
$R^{24}$ represents:
halogen;
straight or branched chain alkyl having from 1 to 12 carbon atoms which may be substituted by one or more halogen atoms:
straight or branched chain alkylsulphonyl having from 1 to 12 carbon atoms which may be substituted by one or more halogen atoms;
or sulphamoyl.

22. The method according to claim 21 wherein $R^{21}$ is selected from the group consisting of ethyl, propyl, butyl, 1-ethylpropyl, 2-methyl-1-propenyl, cyclopropylmethyl and 2-chloroethyl.

23. The method according to claim 21 wherein $R^{22}$ is selected from hydrogen, ethyl and propyl.

24. The method according to claim 21 wherein $R^{23}$ is selected from hydrogen, methyl and unsubstituted amino.

25. The method according to claim 21 wherein $R^{24}$ is selected from methyl, tert-butyl, isopropyl and trifluoromethyl.

26. The method according to claim 20 wherein the dinitroaniline herbicide is selected from the group consisting of
N-butyl-N-ethyl-2,6-dinitro-4-(trifluoromethyl)benzenamine;
N-sec-butyl-4-tert-butyl-2,6-dinitroaniline;
$N^1,N^1$-diethyl-2,6-dinitro-4-trifluoromethyl-m-phenylenediamine;
N-ethyl-N-(2-methyl-2-propenyl)-2,6-dinitro-4 -(trifluoromethyl)benzenamine;
N-(2-chloroethyl)-2,6-dinitro-N-propyl-4 -(trifluoromethyl)aniline;
4-isopropyl-2,6-dinitro-N,N-dipropylaniline;
N-cyclopropylmethyl-2,6-dinitro-N-propyl-4-(trifluoromethyl)benzenamine;
2,6-dinitro-N,N-dipropyl-4-(trifluoromethyl)benzeneamine and
N-(1-ethylpropyl)-3,4-dimethyl-2,6-dinitro(trifluoromethyl) -benzeneamine.

27. The method according to claim 20 wherein for the compound of formula I, n is three and the groups $(R^2)_n$ occupy the 2,3 and 4-positions of the benzoyl ring, $R^2$ being as defined in claim 20.

28. The method according to claim 20 wherein for the compound of formula I, $R^2$ is selected from chlorine, bromine, —S(O)$_p$Me and trifluoromethyl, wherein p is as defined in claim 20.

29. The method according to claim 20 wherein for the compound of formula I, n is two and the groups $(R^2)_n$ occupy the 2- and 4-positions of the benzoyl ring, $R^2$ being as defined in claim 20.

30. The method according to claim 20 wherein for the compound of formula I, one of the groups $R^2$ is $—S(O)_p$Me, wherein p is as defined in claim 20.

31. The method according to claim 20 wherein for the compound of formula I, R is hydrogen.

32. The method according to claim 20 wherein the compound of formula I is selected from the group consisting of
5-cyclopropyl-4-(2-methylsulphonyl-4-trifluoromethyl) benzoylisoxazole;
5-cyclopropyl-4-(4-methylsulphonyl-2-trifluoromethyl) benzoylisoxazole;
4-(2-chloro-4-methylsulphonyl)benzoyl-5-cyclopropylisoxazole;
4-(4-chloro-2-methylsulphonyl)benzoyl-5-cyclopropylisoxazole;
4-(4-bromo-2-methylsulphonyl)benzoyl-5-cyclopropylisoxazole;
ethyl 3-[5-cyclopropyl-4-(3,4-dichloro-2-methylsulphenyl) benzoylisoxazole]carboxylate; and
5-cyclopropyl-4-(3,4-dichloro-2-methylsulphonyl)benzoylisoxazole.

33. The method according to claim 20 wherein the compound of formula I is 5-cyclopropyl-4-(2-methylsulphonyl-4-trifluoromethyl)benzoylisoxazole.

34. The method according to claim 20 wherein from 5 g to 512 g of 4-benzoylisoxazole of formula I and from 150 g to 3000 g of the dinitroaniline herbicide per hectare are applied to the locus.

35. The method according to claim 20 wherein from 20 g to 200 g of 4-benzoylisoxazole of formula I and from 150 g to 2000 g of the dinitroaniline herbicide per hectare are applied to the locus.

36. The method according to claim 20 wherein from 25 g to 150 g of 4-benzoylisoxazole of formula I and from 250 g to 500 g of the dinitroaniline herbicide per hectare are applied to the locus.

37. The method according to claim 20 wherein the 4-benzoylisoxazole of formula I the and the dinitroaniline herbicide are applied pre-emergence of the weeds.

38. The method according to claim 20 wherein the 4-benzoylisoxazole and dinitroaniline herbicide are applied to an area used, or to be used, for the growing of a crop.

39. The method according to claim 38 wherein the crop is sugarcane.

40. The method according to claim 38 wherein the crop is maize.

41. A synergistic herbicidal composition comprising:
(a) a 4-benzoylisoxazole of formula (I):

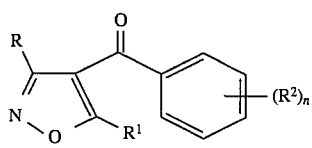

wherein
R is hydrogen or $—CO_2R^3$;
$R^1$ is cyclopropyl;
$R^2$ is selected from the group consisting of halogen, $—S(O)_p$Me, $C_{1-6}$ alkyl and $C_{1-6}$ haloalkyl;
n is two or three;
p is zero, one or two; and
$R^3$ is $C_{1-4}$ alkyl; and
(b) N-(1-ethylpropyl)-3,4-dimethyl-2,6-dinitrobenzeneamine, which is pendimethalin;
in association with one or more members selected from the group consisting of a herbicidally acceptable diluent or carrier and a herbicidally acceptable surface active agent;
wherein the weight ratio of (a):(b) is from 1:6000 to 64:1.

42. A method for controlling the growth of weeds at a locus which comprises applying to the locus a synergistic herbicidally effective amount of:
(a) a 4-benzoylisoxazole of formula (I):

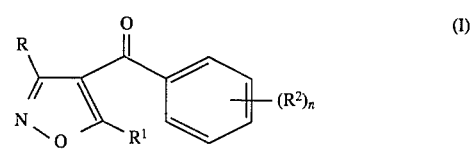

wherein
R is hydrogen or $—CO_2R^3$;
$R^1$ is cyclopropyl;
$R^2$ is selected from the group consisting of halogen, $—S(O)_p$Me, $C_{1-6}$ alkyl and $C_{1-6}$ haloalkyl;
n is two or three;
p is zero, one or two; and
$R^3$ is $C_{1-4}$ alkyl; and
(b) N-(1-ethylpropyl)-3,4-dimethyl-2,6-dinitrobenzeneamine, which is pendimethalin;
wherein from 0.5 g to 512 g of said 4-benzoylisoxazole of formula (I) and from 8 g to 3000 g of pendimethalin per hectare are applied to said locus.

43. A synergistic herbicidal composition comprising:
(a) 5-cyclopropyl-4-(2-methylsulphonyl-4-trifluoromethyl)benzoylisoxazole; and
(b) N-(1-ethylpropyl)-3,4-dimethyl-2,6-dinitrobenzeneamine, which is pendimethalin;
in association with one or more members selected from the group consisting of a herbicidally acceptable diluent or carrier and a herbicidally acceptable surface active agent;
wherein the weight ratio of (a):(b) is from 1:20 to 1:1.33.

44. A method for controlling the growth of weeds at a locus which comprises applying to the locus a synergistic herbicidally effective amount of:
(a) 5-cyclopropyl-4-(2-methylsulphonyl-4-trifluoromethyl)benzoylisoxazole; and
(b) N-(1-ethylpropyl)-3,4-dimethyl-2,6-dinitrobenzeneamine, which is pendimethalin;
wherein from 25 g to 150 g of (a) and from 250 g to 500 g of (b) per hectare are applied to said locus.

* * * * *